United States Patent [19]
Lee

[11] Patent Number: 5,902,609
[45] Date of Patent: May 11, 1999

[54] COMPOSITION FOR THE CONTROL OF WOUND SCAR PRODUCTION

[75] Inventor: Raphael C. Lee, Chicago, Ill.

[73] Assignee: Massachusetts Institute of Technology, Cambridge, Mass.

[21] Appl. No.: 08/740,242

[22] Filed: Oct. 25, 1996

Related U.S. Application Data

[63] Continuation of application No. 08/190,239, Feb. 1, 1994, Pat. No. 5,569,678, which is a continuation of application No. 07/916,412, Jul. 20, 1992, abandoned, which is a continuation-in-part of application No. 07/629,080, Dec. 17, 1990, Pat. No. 5,132,119, which is a continuation of application No. 07/387,604, Jul. 31, 1989, abandoned.

[51] Int. Cl.$^6$ .......................... A61K 33/26; A61K 31/58; A61K 31/55; A61K 31/54
[52] U.S. Cl. .......................... 424/646; 514/171; 514/174; 514/211; 514/225.8; 514/356; 514/648; 514/654
[58] Field of Search .................................... 514/654, 356, 514/211, 171, 174, 225.8, 648; 424/646

[56] References Cited

U.S. PATENT DOCUMENTS

| | | | |
|---|---|---|---|
| 4,690,935 | 9/1987 | Taylor et al. | 514/356 |
| 4,806,464 | 2/1989 | Spelsberg | 435/6 |
| 5,270,171 | 12/1993 | Cercek et al. | 435/29 |
| 5,525,513 | 6/1996 | Chen et al. | 435/320.1 |

FOREIGN PATENT DOCUMENTS

| | | |
|---|---|---|
| 52-025768 | 2/1977 | Japan . |
| 52-083545 | 7/1997 | Japan . |
| WO91/01624 | 2/1991 | WIPO . |

OTHER PUBLICATIONS

Askey et al., "The Effect of Weak Electric Fields and Verapamil on Exocytosis in Human Fibroblasts", *J.Cell.Biol.*, Joint Meeting of American Society for Cell Biol. and American Society for Biochem. and Mol. Bio., San Francisco, CA, abt. #1905, p. 336a, Jan. 29–Feb. 2, 1989.

Askey et al., Weak Electric Fields and Verapamil Reduce Exocytosis in Human Fibroblasts, *Proceedings Electrochemical Society*, Los Angeles, CA, May 7–12, 1989.

Ohmori, S., "Effectiveness of Silastic Sheet Coverage in the Treatment of Scar Keloid (Hypertrophic Scar)," *Aesthetic Plastic Surgery*, 12:95–99 (1988).

Chen et al., "Voltage Sensitive Calcium Channels in Normal and Transformed 3T3 Fibroblasts," *Science*, 239:1024–1026 (1988).

Onuma et al., "Electric Field–directed Cell Shape Changes, Displacement and Cytoskeletal Reorganization Are Calcium Dependent," *J. Cell. Bio.*, 106:2069–2075 (1988).

McLeod et al., "Frequency Dependence of Electric Field Modulaltion of Fibroblast Protein Synthesis," *Science*, 236:1465–1469 (1987).

Abergel et al., "Biochemical Composition of the Connective Tissue in Keloids and Analysis of Collagen Metabolism in Keloid Fibroblast Cultures," *J.Invest. Dermatol.*, 84:384–390 (1985).

Miller, E.A., "Electric Field Modulation of Exocytosis in Human Fibroblasts," B.S. Thesis, Massachusetts Institute of Technology (May, 1987).

Sank et al., "Increased calcium levels alter cellular and molecular events in wound healing", *Surgery* 106 (6):1141–1148 (1989).

Steinleitner et al., "Use of Diltiazem for Preventing Postoperative Adhesions," *J. Reproductive Medicine*, 33:891–894 (1988).

Block et al., "$Ca^2$–channel blockers inhibit the action of recombinant platelet–derived growth factor in vascular smooth muscle cells," *Proc. Natl. Acad. Sci. USA*, 86:2388–2392 (1989).

Lee et al., "Calcium Antagonists Retard Extracellular Matrix Production in Connective Tissue Equivalent," *J. Surg. Res.*, 49:463–466 (1990).

McLeod, K.J., "Modulation of Biosynthesis by Physiologically Relevant Electric Fields," Ph.D. Thesis, Massachusetts Institute of Technology, 1986.

Aggeler, J., "Cytoskeletal Dynamics in Rabbit Synovial Fibroblasts: II. Reformation of Stress Fibers in Cells Rounded by Treatment with Collagenase–Inducing Agents," *Cell Motility and the Cytoskeleton*, 16:121–132 (1990).

Clark et al., "The response of retroperitoneal fibrosis to tamoxifen," *Surgery*, 109:502–506 (1991).

Kinzbrunner et al., "Remission of Rapidly Growing Desmoid Tumors after Tamoxifen Therary," *Cancer*, 52:2201–2204 (1983).

Unemori et al., "Reorganization of Polymerized Actin: A Possible Trigger for Induction of Procollagenase in Fibroblasts Cultured in and on Collagen Gels," *J. Cell Bio.*, 103:1021–1031 (1986).

Smedley et al., "Effect of calmodulin inhibitors on wound healing in Xenopus early embryos," *Cytobios.*, 42:25–32 (1985).

Cohen et al., "Collagen Synthesis in Keloid and Hypertrophic Scar Following Intralesional Use of Triamcinolone," *Surg. Forum*, 24:521–3 (1973).

Salmela, K., "Comparison of the Effects of Methylprednisolone and Hydrocortisone on Granulation Tissue Development," *Scand. J. Plast. Reconstr Surg*, 15:87–91 (1981).

Van Bocksmeer et al., "Models for Assessing Scar Tissue Inhibitors," *Retina*, 5:47–60 (1985).

(List continued on next page.)

*Primary Examiner*—William R. A. Jarvis
*Attorney, Agent, or Firm*—Hamilton, Brook, Smith & Reynolds, P.C.

[57] ABSTRACT

This invention pertains to a composition for controlling wound scar production containing a calcium antagonist and a protein synthesis inhibitor. The method can be used to minimize wound scars, such as hypertrophic wound healing disorders keloids and burn scar contractures in humans or other mammals, particularly those individually prone to excesssive scarring Calcium antagonist treatment can also be used to control diseases associated with excessive scarring. such as cirrhosis of the liver, constructive pericarditis Dupuytren's disease of the hand, plantar fibrosis of the foot, and various other fibromatoses.

5 Claims, 5 Drawing Sheets

OTHER PUBLICATIONS

Lotif et al., "Mesenteric fibromatosis complicating familial adenomatous polyposis: predisposing factors and results of treatment," *Int. J. Colorect Dis.*, 4:30–36 (1989).

Massoud, E., "Traitement des chéloides et des cicatrices hypertophiques par la triamcinolone acétonide," *Ann. Chir. Plast.*, 15(1):54–56 (1970).

Berkow et al., "The Merck Manual of Diagnosis and Therapy," Merck Sharp & Dohme Research Laboratories, Rayway, NJ, p. 2306 (1987).

Lipton et al., "Calcium antogonism by the antioestrogen tamoxifen," *Cancer Chemother. Pharmacol.*, 18(1):17–20 (1986).

McGonigan et al., "The effects of breast cancer chemotherapy on wound healing in the rat," *J. Surg. Res.*, 42(5):560–564 (1987).

Lossnitzer et al., Prevention of Myocardial Cell Necrosis in the Syrian Hamster—Results of Long–Term Treatment, In *Hypertrophic Cardiomyopathy: Ther. Role Calcium Antagonists*, Kaltenbach et al., eds. pp. 99–114 (1982).

COMPOSITION FOR THE CONTROL OF WOUND SCAR PRODUCTION

This application is a continuation of co-pending application Ser. No. 08/190,239 filed Feb. 1, 1994, now U.S. Pat. No. 5,569,678 which is a File Wrapper Continuation of U.S. Ser. No. 07/916,412, filed Jul. 20, 1992 (abandoned), which is a Continuation-in-Part application of U.S. Ser. No. 07/629,080, filed Dec. 17, 1990 (issued as U.S. Pat. No. 5,132,119 on Jul. 21, 1992), which is a File Wrapper Continuation of Ser. No. 387,604, filed Jul. 31, 1989 (abandoned), the entire teachings of which are incorporated herein by reference.

BACKGROUND OF THE INVENTION

The ability to heal by forming scars is essential for mammalian systems to survive wounding after injury. Normally, wound healing is a continuous process extending over a one-to-two-year period The process can be conceptually divided into three fundamentally distinct stages. The first stage is an intensely degradative phase called the inflammatory stage It occurs immediately after injury and provides a leans to remove the damaged tissues and foreign matter from the wound. Two-to-three days later, as fibroblasts from the surrounding tissue move into the wound, the repairing process enters its second stage, the proliferation and matrix synthesis stage. The fibroblasts in the wound proliferate and actively produce macromolecular such as collagen and proteoglycans, which are secreted into the extracellular matrix. The newly-synthesized collagen fibrils are cross-linked by lysyl oxidase and provide structural integrity to the wound. During this stage, fibroblasts also contract the intact collagen in order to reduce the surface area of the wound. This second stage lasts about three weeks. In the final, remodeling stage, the previous randomly-organized collagen fibril is aligned in the direction of mechanical tension and becomes more organized so that the mechanical strength of the wound area can be increased. The repair process is accomplished when the chemical and physical barrier functions of the skin are restored.

Normal wound healing follows a well-regulated course. However, imbalances may cause abnormal scars to form. For example if the biosynthetic phase continues longer than necessary or degradation of collagen decreases, hypertrophic scars may form. These scars cause problems ranging from aesthetic deformity to severe limitation of motion. Hypertrophic scars more frequently occur among children and adolescents, suggesting that growth factors may influence the development of this type of scar.

Hypertrophic scars are especially common in patients who have burns or wounds that heal by secondary intention. Another type of excess scar is the keloid. In this disorder, the cells appear to lace sensitivity to normal feedback signals. They are larger than hypertrophic scars and grow in an unregulated way, tending to invade normal tissue surrounding the wound. They rarely disappear spontaneously and often recur after surgical excision. The management of these scars remains a major unsolved clinical problem.

Existing therapy for hypertrophic scars and keloids includes surgery, mechanical pressure, steroids, x-ray irradiation and cryotherapy. There are many disadvantages associated with each of these methods. Surgical removal of the scar tissue is often incomplete and can result in the development of hypertrophic scars and keloids at the incision and suture points. Steroid treatments are unpredictable and often result in depigmentation of the skin. X-ray therapy is the only predictably effective treatment to date. However, because of its potential for causing cancer, it is not generally recommended or accepted.

Compositions comprising tripetidese tetrapeptides and pentapeptides have been shown to inhibit biosynthesis of collagen and may be used to treat diseases caused by excess accumulation of collagen (Mitsubishi Chem., Japanese Patent Nos. 52083545, Jul. 12, 1977, and 52025768, Feb. 25, 1977). The effects of applying silastic sheets onto the surface of hypertrophic scars was studied and shown to shrink and soften scar tissue. [Ohmori, S. *Aesthetic Plastic Surgery* 12: 95–99 (1988)].

Despite the various treatments presently available, there is no widely accepted and predictably effective means for preventing or treating wound scars, such as hypertrophic scars or keloids.

SUMMARY OF THE INVENTION

This invention pertains to a method for minimizing or preventing excessive scar formation, particularly hypertrophic wound healing disorders, such as hypertrophic s cars and keloids. Specifically, the method comprises administering an effective amount of a calcium antagonist, to a wound site for a period of time sufficient to minimize the scar, or to prevent the formation of a hypertrophic scar. Preferably, the calcium antagonist is selected from phenylalkylamine compounds, such as verapamil; biologically compatible polyvalent ionic salts, such as cobalt chloride and nickel chloride; dihydropyridine compounds, such as nifedipine, nicardipine and nimodipine; benzothiazepine compounds, such as diltiazem; and phenothiazines, such as trifluoperazine and tamoxifen. The calcium antagonist can be administered alone or in combination with a protein synthesis inhibitor (e.g., steroids) as part of a complete therapeutic regimen. For example, the steroid can be selected from the corticosteroids and glucocorticosteroids, such as triamcinolone acetonide. For similar purposes vitamin E can be co-administered. The calcium antagonist is applied to the wound sites such as by injecting it directly irto a scar or topically applying it onto the wound sites If a steroid or vitamin E is used in conjunction with the calcium antagonist, the steroid can be co-administered or applied subsequently to the wound sites preferably within a two week time period. The steroid is also administered directly to the wound site; it may be injected or topically applied. In whatever manner they are administered, the calcium antagonist and/or the steroid can be admixed with a pharmaceutically acceptable vehicle to facilitate localization of the agent to the wound site. similarly, a non-steroidal anti-inflammatory agent can be co-administered with the calcium antagonist The drugs may be put into sustained release capsules to provide continuous treatment at therapeutic doses without systemic side effects.

The method of the present invention can be used to minimize or prevent scar formation, such as hypertrophic wounds, keloids and burn scar contractures, in humans or other mammals, particularly those individuals prone to excessive scarring. A calcium antagonist, alone or in combination with or followed by a steroid or vitamin E, can be applied to a presently existing hypertrophic scar to reverse the scarring process and essentially eliminate the scar tissue. The present invention can also be used therapeutically to control diseases associated with excessive scarring, such as cirrhosis of the liver, constrictive pericarditis, Dupuytren's disease of the hand, plantar fibrosis of the foot and various other fibromatoses.

DETAILED DESCRIPTION OF THE INVENTION

Figure 1A:
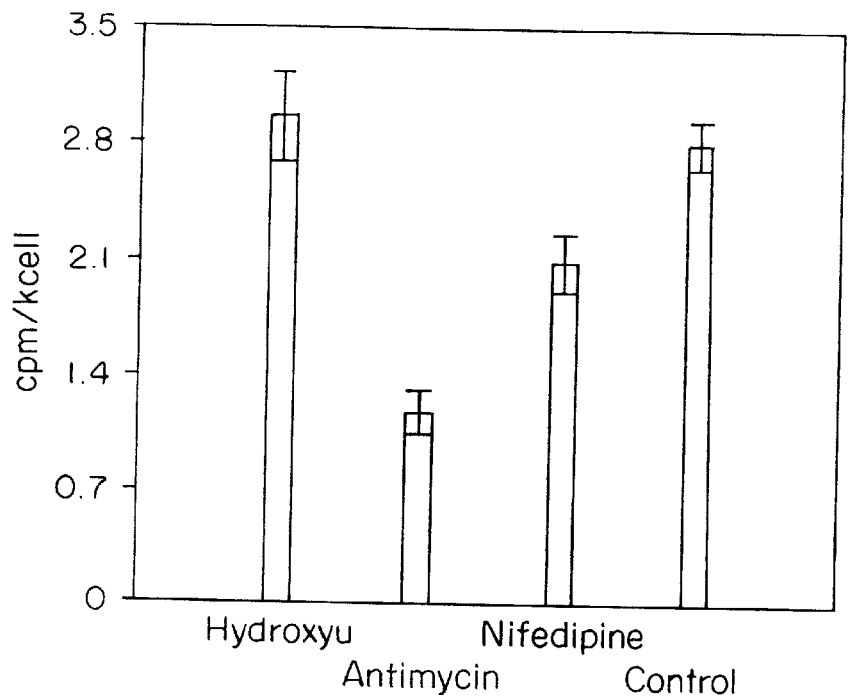
FIGS. 1a and 1b are graphic representations of the effects of hydroxyurea (7.9 mM), antimycin A (1.0 $\mu$M) and nifedipine (100 $\mu$M) on the rate of proline incorporation (FIG. 1a) or rate of sulfate incorporation (FIG. 1b) into fibroblast populated collagen matrices (FPCM) bathed in DMEM/5.5 $\mu$M fructose.

Calcium antagonists, as used herein, are compounds which can interfere with calcium transport within a cell or block/inhibit one or more events involved in the calcium cascade. Several classes of calcium antagonists, include calmodulin inhibitors, Protein Kinase C inhibitors and calcium transport blockers. Calmodulin inhibitors prevent the binding of calcium to calmoduline thereby interrupting intracellular signal transduction, including activation of Protein Kinase C, the next event in the calcium cascade. Compounds that inhibit Protein Kinase C or other downstream events can be used. Calmodulin inhibitors include phenothiazines, such a trifluoperazine and tamoxifen (also Protein Kinase C inhibitors). Calcium transport blockers, also called calcium entry antagonists, calcium channel antagonists or calcium channel blockers, block the action of calcium channels, which are regions of cell membranes that facilitate the transport and secretion of fluids and electrolytes such as calcium into the cell [Rasmussen, It. N.E.J. Med. 314: 1094–1101 (1986)]. Compounds included in this class are phenylalkylamine compounds, such as verapamil; polyvalent ionic salts that physically block the calcium channels, such as nickel chloridea cobalt chloride and other biologically acceptable salts of these; hydropyridine compounds, such as nifedipine; and benzothiazepine compoundse such as diltiazem. Other compounds that affect the secondary messenger pathways in cellular signal transduction may have the same or similar effect as calcium antagonists on cell shape and tissue remodeling.

The present invention stems from the discovery that calcium antagonists which interfere with calcium metabolism or transport across the cell membrane, can inhibit exocytosis in fibroblast cells; can retard biosynthesis of collagen and sulfated glycosaminoglycans (GAG); can be used to decrease the collagen content of the extracellular matrix; and can also stimulate increased collagenase activity, leading to softening of the scar tissue. These features work together to control wound scar production; by minimizing, preventing or reversing the scarring process, depending upon the course of the disease or type of wound treated.

Exocytosis, a process involved in cellular secretion of protein, is but one mechanism affected by calcium antagonist treatment. During secretion, vesicles that contain sorted and concentrated protein pinch off from the Golgi apparatus and move toward the cell membrane at the leading edge of the call, where they fuse with the cell membrane and release protein into the extracellular space. This process of fusion and release is known as exocytosis and is one of the essential steps in secretion of extracellular matrix macro-molecules (such as glycosaminoglycanse collagen and elastin). Many diseases and disorders are characterized by excessive biosynthesis or secretion. For example, hypertrophic wound healing disorders are characterized by over-secretion of protein and collagen This overproduction is one factor which contributes to excessive scarring or keloid formation.

It has also been observed that calcium antagonist regulate cell shape. As described in detail in the exemplification, fibroblasts that have been treated with a calcium antagonist became more rounded than untreated fibroblasts. The treated cells were tested for viability and were found to have intact cell membranes which are indicative of viable cells. The observation that treated fibroblast cells become alteration was correlated with changes in cell programming from a biosynthetic mode (mechanism normally undertaken by untreated fibroblasts) to a degradative mode. It is believed that this change toward matrix degradations mediated by cell shape changes, plays a roll in controlling wound scar production. Thus, other compounds can be studied for their ability to regulate (up regulate or down regulate) fibroblast biosynthesis by observing their interaction with calcium antagonists.

In a preferred embodiment, wound scar content can be minimized by administering an effective amount of a calcium antagonist to a hypertrophic wound site. The calcium antagonist may be administered alone, or in combination with or followed by the administering of a protein synthesis inhibitor (e.g., steroid). For example, a steroid can be co-administered with the calcium antagonist, or applied separately, preferably within a two-week interval following the application of the calcium antagonists. Treatment of the wound site with the calcium antagonist, with or without the steroid, should continue for a period of time sufficient to minimize the wound area. Suitable calcium antagonists include, but are not limited to phenylalkylamine compounds, such as verapamil; biologically acceptable polyvalent salts, such as cobalt chloride and nickel chloride; hydropyridine compounds, such as nifedipine, nicardipine and nimodipine; and phenothiazines, such as trifluoperazine and tamoxifen which are examples of calmodulin inhibitors. The amount of calcium antagonist which can be effectively administered is dependent upon the type of calcium antagonist used and the scar site to be treated, and can be ascertained by monitoring the scar site during treatment. The amount can be adjusted accordingly depending upon the response observed. Threshold effective amounts of verapamil and nifedipine are approximately 10 μM and 1 mM, respectively. Steroids which may be used include, but are not limited to; corticosteroids and glucocorticosteroids, such as triamcinclone acetonide (also known as KENALOG™), and Vitamin E (α-gtocopherol) (Ehrlich et al. 1972, *Ann. Surg.* 75:235). The amount of steroid which can be effectively administered will depend upon the type of steroid used. The threshold effective amount of triamcinolone acetonide is approximately. The effects of calcium antagonist treatment, with and without steroids, on various types o wound scars are illustrated in the exemplification.

Hydropyridine compounds such as nifedipine are relatively insoluble in aqueous solution. Due to their insolubility, it may be advantageous to solubilize the drug in a non-polar carrier depending upon the location of the disorder to be treated. Calcium antagonists can be administered to a wound site either alone or they can be admixed with pharmaceutically acceptable vehicles to facilitate their diffusion into the wound site. One suitable vehicle is dimethyl sulfoxide in a physiologically acceptable amount. Calcium antagonists can be incorporated into liposomes for localization of concentrated quantities of the drug, as well as for the sustained release of the drug to the wound site.

Calcium antagonists can be concentrated and incorporated into controlled release polymers as an alternative mode of administering the drug (e.g., transdermal administration). Examples of controlled release polymers have been described by Folkman and Langer, U.S. Pat. No. 4,391,727, issued Jul. 5, 1983; Yolles, U.S. Pat. Nos. 3,880,991 issued Apr. 29, 1975, and 3,887,699, issued Jun 3, 1975; Boswell, U.S. Pat. No. 3,773,919, the teachings of which are incorporated herein by reference. Preferably, biodegradable polymers will be used.

The method of administering an acceptable dose of calcium antagonist to minimize scarring is dependent upon the location of the hypertrophic wound and the extent of scarring. In particulars the calcium antagonist, either alone or in combination with a pharmaceutically acceptable vehicle, can be topically applied to the surface of the wound sites; it can be injected into the wound site; or it can be incorporated into a controlled release polymer and surgically implanted in a region to be treated. Surgical implantation is advantageous for treating disorders such as cirrhosis of the liver and constrictive pericarditis. This permits the calcium antagonist to be localized in the diseased site without adversely affecting the patient or releasing excessive amounts of the drug into the circulation system. If a steroid is used in conjunction with, or following, the calcium antagonists the acceptable dose of steroid may be administered through several methods. The steroid, either alone or in combination with a pharmaceutically acceptable vehicle, can be topically applied to the surface of the wound site; injected into the wound site; or incorporated into a controlled release polymer and surgically implanted into the region to be treated.

Depolymerization of cycloskeletal proteins leading to alteration of cell shape and matrix degradation can be regulated using the methods of this inventions. Secondary to this, the invention can be used to regulate and block exocytosis. In particulars, fibroblasts are contacted with an effective amount of a calcium antagonist sufficient to degrade the matrix and retard exocytosis to a desired degree. The method of contacting the calcium antagonists to the fibroblast cells of interest and the effective amount of these drugs are described above.

In addition to treating hypertrophic wound healing disorders, one or combinations of several different calcium antagonists co-administered to a patient can be used to therapeutically control diseases caused by excessive fibroblast biosynthesis. Diseases characterized by fibroblast overproduction include, cirrhosis of the liver, constrictive pericarditis, Dupuytren's disease of the hand, as well as other fibromatose. While these are but a few diseases which can be treated using the methods of this invention, it should be recognized that any disease which is characterized by excessive fibroblast biosynthesis can be treated using calcium antagonists.

The invention is further illustrated by the following Examples which should not be construed to be limiting in any way:

EXAMPLE 1

Studies on Protein and GAG Secretion
Tissue Preparation

A connective tissue model of uniaxially oriented cells and extracellular matrix Was fabricated using bovine fibroblasts, rat tail tendon collagen and nutrient media. Bovine fascial fibroblasts were harvested from the thigh of freshly slaughtered 2 week old calves (Trelegan's, Cambridge, Mass.) by enzymatic digestion using 0.1% type II collagenase (Worthington Biochemical, Inc., Freehold, N.J.) digestion in Dulbecco's Modified Eagle Medium (DMEM; Gibco, Grand Island, N.Y.) at 37° C. for 4 hours. The released cells were seeded onto tissue culture dishes with DMEM supplemented with 10% NuSerum™ (Collaborative Research, Bedford, Mass.). The media was changed every 48 hours. The cells were passaged once and then either used immediately or stored frozen in 50% calf serum/45% DMEM/5% DMSO at −100° C. When frozen cells were used they were quickly thawed, sedimented through a column of 50% serum/50% DMEM at 185 g for 3 minutes, then plated on coverslips. The media was changed after cell attachment (~4 hours).

Native type I collagen was extracted from rat tail tendon and purified using a modification of the method of Chandrakasan, G. et al., *J. Biol. Chem.* 251: 6062–6067 (1976). Specifically, rat tail tendons were removed from adult Sprague-Dawley rat tails, washed in PBS and distilled water. The tendons were then placed in a solution of 0.05M (3%) acetic acid at the ratio of 200 ml per tail. The mixture was stirred for 96 hours at 8° C.

After 24 hours of stirring, the mixture was filtered through several layers of cheese cloth and then centrifuged at 12000 g (9000 rpm in Sorval GS-3 rotor) for 2 hours. The supernatant was precipitated and redissolved in cold acid multiple times to remove non-collagenous proteins. The collagen solution was sterilized in 1/1000 (v/v) chloroform. This procedure preserves the native structure of the collagen molecule.

Oriented tissue equivalents were made by mixing bovine fibroblasts with a 0.2% collagen solutions 20% calf serum, 10 mg/ml gentamycin solution, 5 mg/ml ascorbate in DMEM as previously described [McLeod, K. J. "Modulation of Biosynthesis by Physiologically Relevant Electric Fields" Ph.D. Thesis M.I.T. 1986]. This suspension was poured into sterile tissue culture dishes containing two sterile porous polyethylene posts held 2 centimeters apart. The dishes were placed in a cell culture incubator gassed at 5% $CO_2$ with 99% humidity. The suspension gelled at 37° C.

Over several days, the fibroblasts remodelled and consolidated the collagen gel around the fixed posts. The resultant oriented fibroblast populated collagen matrix (FPCM) formed a tissue equivalent structure which histologically resembled a ligament. Oriented tissue equivalents are further described in McLeod et al., *Science* 236: 1465–1469 (1987) and in U.S. patent application Ser. No. 07/349,855, filed May 10, 1989, to R. C. Lee and D. Huang, the teachings of which are herein incorporated by references.

Assay for Determining Biosynthetic Activity

Protein and glycosaminoglycan (GAG) biosynthesis was measured using radiolabeled precursors of protein and sulfated GAGs. Four days after casting of the FPCM, the media bathing the ligament equivalents was changed to serum free DMEM with 0.5 mM L-proline (Sigma, St. Louis, Mo.). After 12 hours, the media was changed again to fresh serum-free media supplemented with 10 $\mu$Ci/ml $Na_2^{35}SO_4$ (NEX-041, New England Nuclear, Boston, Mass.), 10 $\mu$Ci/ml L-[5-$^3$H]-proline (NET-573, New England Nuclear, Boston, Mass.) and 0.5 mM L-proline. The samples were bathed in the radiolabeled media for 12 hours. The radiolabeled sulfate was incorporated into GAGs and $^3$H-proline into proteins, and so provided markers of sulfated GAGs and protein synthesis, respectively. Since DMEM is proline-free, the addition of non-radioactive proline ensures a relatively constant specific activity in the medium.

Effect of Calcium Antagonists on Biosynthesis

The effect of calcium antagonists on protein and glycosaminoglycan (GAG) biosynthesis was measured in FPCMs under several conditions. The biosynthetic responses to calcium antagonism were studied in FPCMs cultured in DMEM supplemented with either 5.5 $\mu$M glucose or 5.5 $\mu$M fructose. Both were studied because energy metabolism of cultured fibroblasts is primarily anaerobic when the carbohydrate energy source is glucose and predominantly aerobic when the carbohydrate source is fructose [Thilly, W. G., *Mammalian Cell Technology*, Chapter 5, Butterworth Publishers, Boston, (1986)]. In vivo fibroblasts are, however, believed to derive their energy primarily through aerobic glycolysis.

The drugs used to antagonize calcium channels were verapamil, nifedipine, cobalt chloride and trifluoperazin. Control studies were performed to test the metabolic state of the cells in the FPCM. The effect of hydroxyurea and antimycin A, a drug which blocks oxidative phosphorylation, on biosynthesis was measured in FPCMs cultured in fructose or glucose.

Results

Energy Metabolism

Figure 1B:
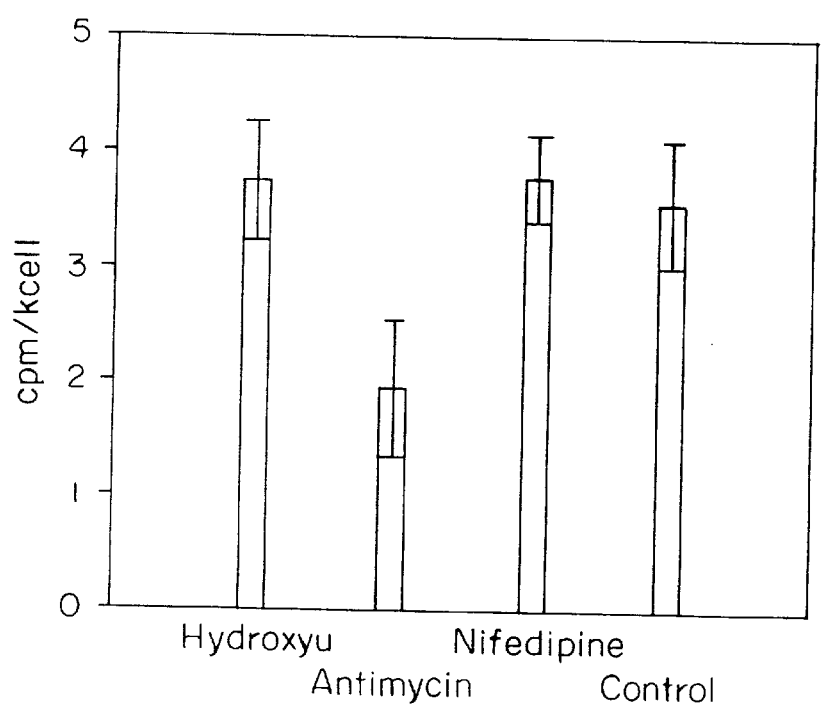

As previously reported [Thilly, W. G., *Mammalian Cell Technology*, Chapter 5 Butterworth Publishers, Boston, (1987)], differences between cellular energy metabolism of fibroblasts provided with glucose or fructose as energy substrates were observed. The effects of antimycin A on both incorporation of proline into extracellular matrix protein and incorporation of sulfate into extracellular matrix glycosaminoglycans over a 12 hour period was measured in FPCMs bathed in DMEM/5.5 mM fructose and their results are shown in FIGS. 1*a* and 1*b*, respectively. Antimycin A had little effect on $^3$H-proline incorporation with FPCMs provided with glucose. In contrast, antimycin A caused a substantial reduction in the rate of proline incorporation into the extracellular matrix in FPCMs provided with fructose.

Protein and Glycosaminoglycan Biosynthesis

Figure 2A:
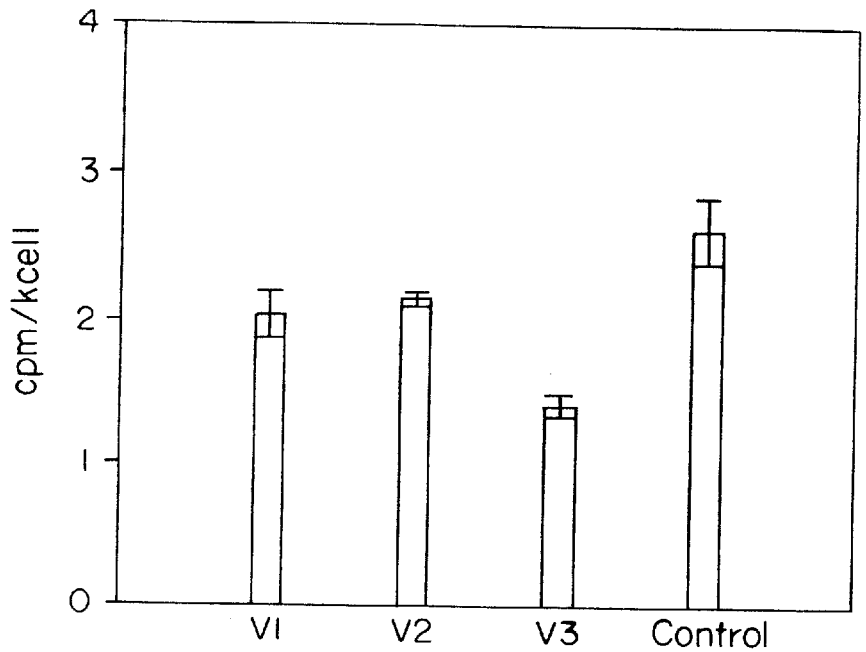
FIGS. 2a and 2b are graphic representations of the dose-dependent effect of verapamil on the rate of proline incorporation of FPCM bathed in DMEM/5.5 $\mu$M glucose and 5.5 $\mu$M fructose, respectively. V1 represents 1 $\mu$M verapamil, V2 represents 10 $\mu$M verapamil and V3 represents 100 $\mu$M verapamil.
Figure 2B:
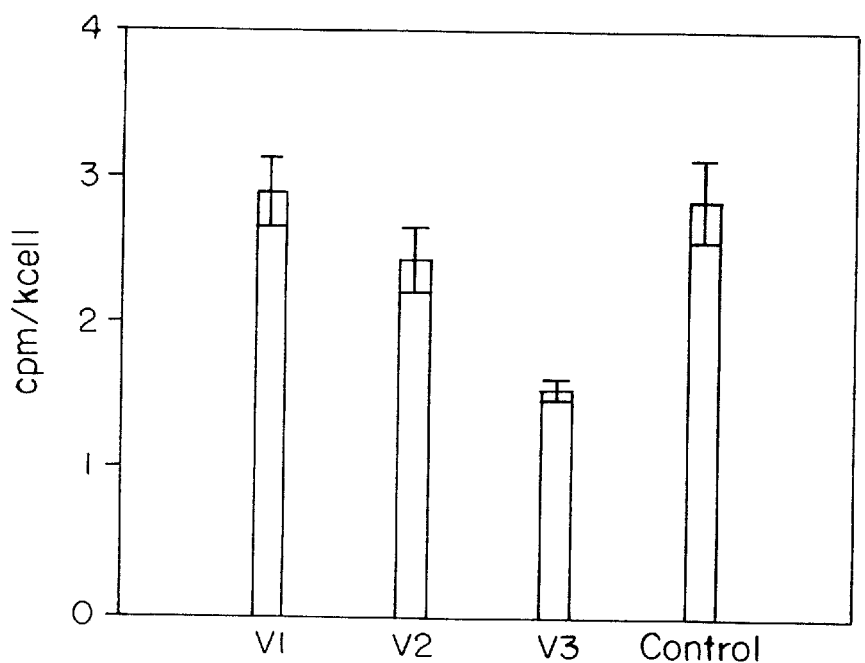

When the effect of the carbohydrate source on the rate of biosynthesis of protein and glycosaminoglycan was examined in FPCMs bathed in DMEM/0.5 mM cold proline, no difference was observed between control FPCMs in glucose or fructose (FIG. 2). There was a dose-dependent effect of verapamil on protein incorporation. However, the biosynthetic response to calcium channel blockaid was observed to depend on the type of calcium antagonist used and whether the carbohydrate source was glucose or fructose.

Figure 3A:
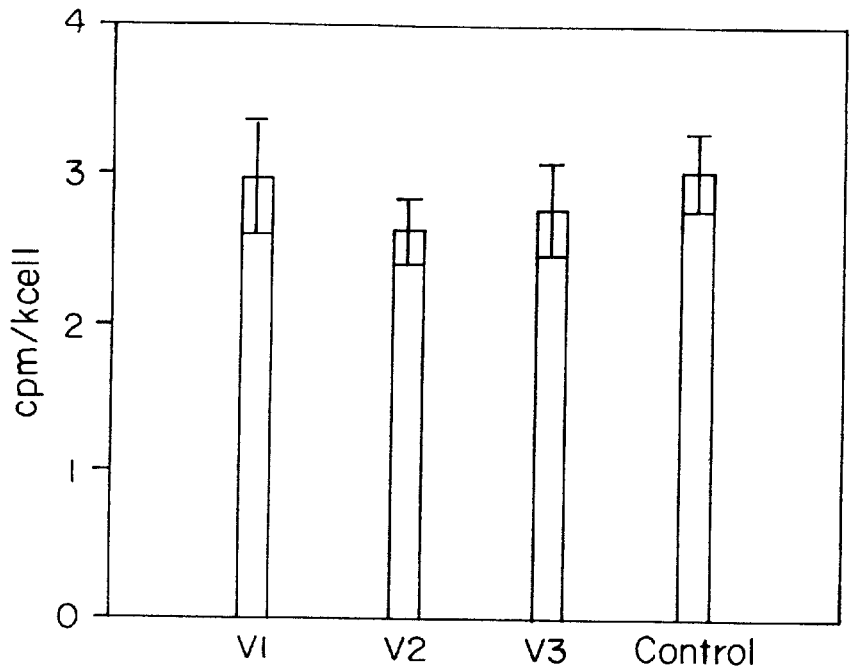
FIGS. 3a and 3b are graphic representations of the effects of verapamil on the rate of sulfate incorporation into glycosaminoglycans in FPCM bathed in DMEM/5.5 $\mu$M glucose and fructose, respectively. V1 represents 1 $\mu$M verapamil, V2 represents 10 $\mu$M verapamil and V3 represents 100 $\mu$M verapamil.
Figure 3B:
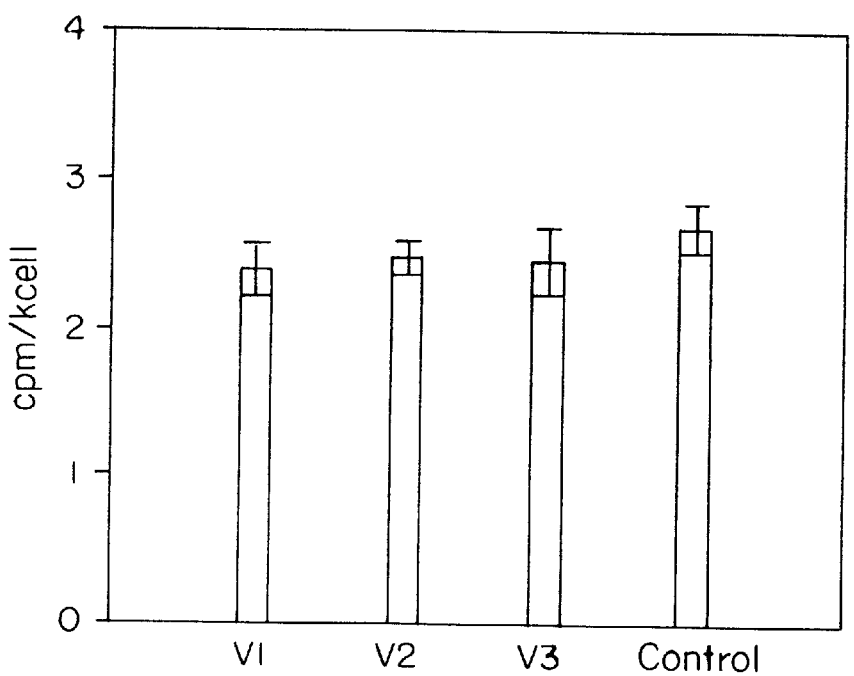

Verapamil retarded the incorporation of $^3$H-proline into the extracellular matrix in the presence of either glucose or fructose (FIG. 2). However, fibroblasts appeared to be more sensitive to verapamil when glucose was used as the metabolic energy source. Verapamil at 100 $\mu$M concentration reduced the $^3$H-proline incorporation by almost 50% in FPCMs provided with either glucose or fructose. Verapamil had no significant effect on sulfated glycosaminoglycan biosynthesis, even at a concentration of 100 $\mu$M (FIG. 3). The lack of effect on GAG biosynthesis incorporation indicated that the verapamil did not reduce cell viability.

In equimolar concentrations, nifedipine caused a larger reduction of $^3$H-proline incorporation than verapamil. As for verapamil, nifedipine at 100 $\mu$M concentration had no effect on GAG biosynthesis. When the medium was supplemented with fructoses nifedipine at 10 and 100 $\mu$M reduced both proline and sulfate incorporation by 60% In contrast, nifedipine at 1 $\mu$M had no effect on either proline or sulfate incorporation. In a series of 3-week-old FPCMs, twelve hours' incubation in 100 $\mu$M nifedipine caused complete digestion of the matrix.

When glucose was used as the carbohydrate source, verapamil at 100 $\mu$M concentration was also found to retard the incorporation of $^3$H-proline into the extracellular matrix about 50%. In fact, fibroblasts appeared to be more sensitive to verapamil when glucose was used as the carbohydrate source. The incorporation of $^3$H-proline in the samples treated with 1 and 10 $\mu$M verapamil was about 20% less than that of the control. Different concentrations of verapamil also had no effect on sulfated GAG biosynthesis. In summary, it was observed that verapamil and nifedipine at 100 $\mu$M each reduced $^3$H-proline incorporation by almost 50–60 in the tissue equivalent.

The rates of $^3$H-proline and sulfated glycosaminoglycan incorporation in fibroblast populated collagen matrices bathed in DMEM/5.5 $\mu$M glucose or fructose and a calcium antagonist are shown in Table 1.

50 mg/ml of cobalt chloride had a profound effect in reducing the rate of protein biosynthesis and increasing the rate of secretion of sulfated glycosaminoglycans, as compared with the effects of verapamil.

TABLE I

|  | Glucose (5.5 $\mu$M) | | Fructose (5.5 $\mu$M) | |
|  | | Glycosaminoglycans (sulfated) | | Glycosaminoglycans (sulfated) |
|  | $^3$H-Proline | (cpm/1 × $10^3$ cells) | $^3$H-Proline | (cpm/1 × $10^3$ cells) |
| --- | --- | --- | --- | --- |
| Control | 1.00 ± 0.04 (16) | 1.00 ± 0.03 (16) | 1.00 ± 0.05 (16) | 1.00 ± 0.04 (16) |
| Verapamil (1 $\mu$M) | 0.85 ± 0.02 (16) | 1.02 ± 0.03 (16) | 1.02 ± 0.02 (16) | 1.00 ± 0.04 (16) |
| Cobalt (50 $\mu$g/ml) | 0.79 ± 0.01 (16) | 1.14 ± 0.03 (16) | 0.90 ± 0.03 (16) | 1.01 ± 0.02 (16) |

In order to identify whether the decrease in the incorporation of radioisotopes into the matrix was due to the inhibition of cell propagation in the FPCMs, hydroxyurea was used to block DNA synthesis. Hydroxyurea prevents the formation of deoxyribonucleotides. The results showed that there was no effect on hydroxyurea on the $^3$H-proline and $^{35}$S-sulfate incorporation in either carbohydrate source.

Figure 6:
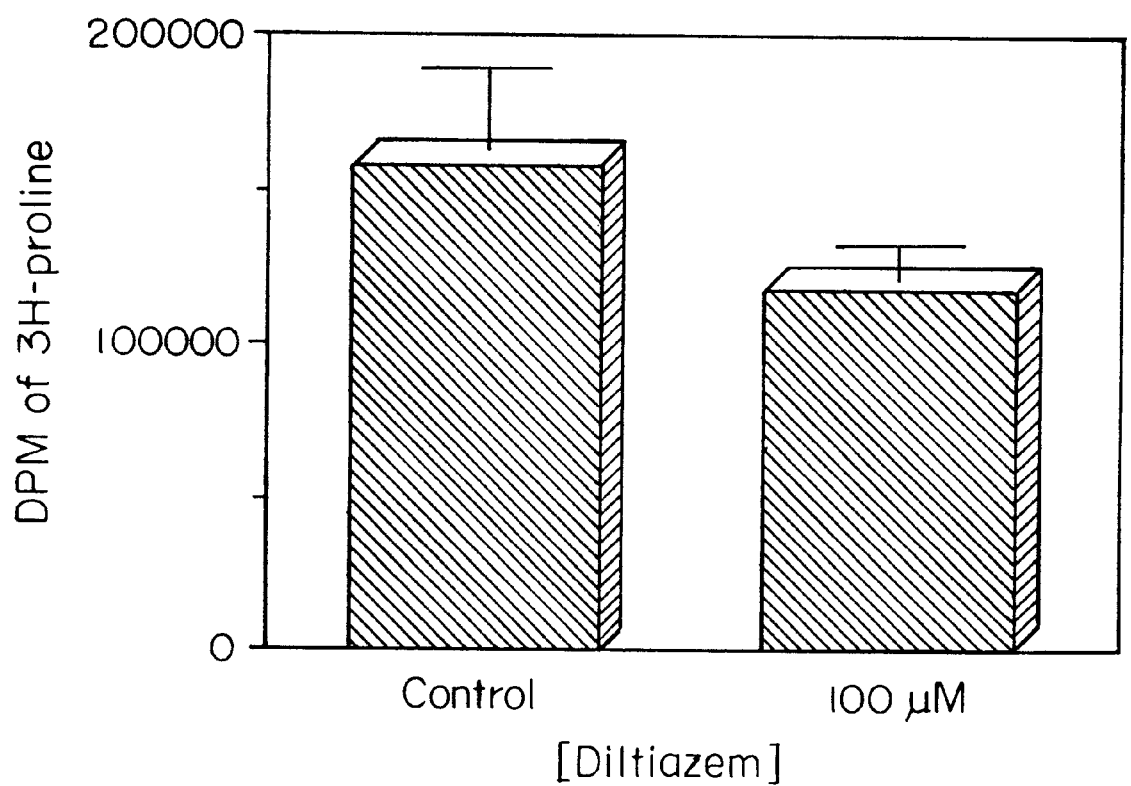
FIG. 6 is a graphic representation of the incorporation of $^3$H-proline into FPCM extracellular matrix. FPCM bathed in fructose were untreated (control) or treated with 100 $\mu$M diltiazem.

The effects of other calcium antagonists have been studied. Preliminary data showed tht 100 $\mu$M ditiazen reduced $^3$H-proline incorporation by about 30% in the connective tissue equivalent. See FIG. 6. Trifluoperazine has also been studied.

EXAMPLE 2

Effect of Calcium Antagonist on Cell Membrane Channels and Transporters other Than Calcium Ion Channels The effects of verapamil and nifedipine at 100 $\mu$M concentration on cell membrane channels and transporters other than calcium channels were studied. The purpose of the study was to determine whether decreases in the incorporation of radioisotopes in the FPCM matrix is due to decreased uptake of the cell generally or whether calcium channels are involved independently form the other transporters on the cell membrane.

To determine if this was the mechanism, glutaraldehyde was used to crosslink all the amino acid transporters on the cell membrane before and after the cells were treated with calcium antagonists. Fibroblasts were grown on four different sets of culture dishes. Set one was the control. Cells were labeled with $^3$H-proline for 20 minutes and then they were treated with 3.7% glutaraldehyde (final concentration) for two hours. Set two was first treated with glutaraldehyde for two hours and then were labeled with $^3$H-proline for 20 minutes. This was to see whether glutaraldehyde could completely block the amino acid transporters on the cell membrane so that no $^3$H-proline could enter the cells. That also means no $^3$H-proline could leave the cells once they were labeled with radioisotopes and treated with glutaraldehyde. Fibroblasts in sets three and four were treated with different calcium antagonists during the 20-minute radiolabeling period. Then, with the same procedure as set one, they were treated with glutaraldehyde for two hours. Before the cell membranes were broken down by papain, cells were washed 5 times with 20 ml phosphate-buffered saline to get rid of the free labels on the cell surface and between cells. Aliquots of 1 ml papain-digest were counted for tritium radioactivity The result showed that neither verapamil nor nifedipine at 100 $\mu$M concentration significantly hindered the uptake of $^3$H-proline into the cells.

EXAMPLE 3

Studies on Exocytosis

Human Fibroblast Cell Culture

Human neonatal foreskin fibroblasts were harvested from newborns at the time of circumcision at the Brigham and Women's Hospital. The samples were initially placed in antibiotic supplemented Dulbecco's Modified Eagles Media (DMEM) then incubated in trypsin for 20 minutes to remove the surface epithelial layer. The tissue was then washed in Phosphate-Buffered Saline (PBS) solutions then centrifuged at 180 g for 5 minutes to separate the epidermal cells. The dermis was minced then subjected to 0.1% type II collagenase (Worthington Biochemical Inc., Freehold, N.J.) digestion in DMEM for 4 hours. The released cells were seeded onto tissue culture dishes with DMEM supplemented with 10% NuSerum™ (Collaborative Research, Bedford, Mass). The media was changed every 48 hours. The cells were passed once and then were either used immediately or stored frozen in 50% serum/45% DMSO at −100° C. When frozen cells were used they were quickly thawed, sedimented through a column of 50% serum/50% DMEM at 185 g for 3 minutes, then plated on coverslips. The media was changed after cell attachment (~4 hours).

Quantification of Dye Release

To determine if the rate of fluid phase exocytosis was modulated by calcium antagonists, the rate of exocytosis in human fibroblasts was measured using the rate of release of Lucifer yellow labeled dextran (LYD, M.W. 10,000) (Molecular Probes Inco, Portland, Oreg.), from vesicles in the cytoplasm of human foreskin fibroblasts. The LYD was loaded into cells by fluid phase pinocytosis (endocytosis) in the absence of serum. The intracellular location and transport of the dye was monitored under control and experimental conditions using video image analysis.

$P_2$–$P_5$ fibroblast cells were harvested from monolayer by brief 1x trypsin and ethylenediaminetetraacetic acid (EDTA) digestion, plated on glass coverslips and allowed to become 50% confluent. Cell laden coverslips (CLCS) were bathed in DMEM supplemented with 5 mg/ml Lucifer Yellow CH Dextran (LYD) for 12 hours under standard conditions. The CLSC were then washed five times in PBS at 37° C. to remove extracellular LYD, then placed in 60 mm sterile cell culture dishes. The dishes contained serum free DMEM at 37° C. supplemented with either verapamil (10 $\mu$M), or no drug (control) The dishes were returned from each of the dishes after 0, 2, 4 and 6 hours. They were quickly immersed in neutral buffered formalin at 8° C. allowed 20 minutes to fix, then the CLCS were mounted on glass microscope slides. The mounting solution was 50% glycerol, NaF phenylaminediamine.

Each cell to be analyzed was placed in the center position within the field of view. The LY fluorescence was excited by filtered 100 watt mercury arc lamp illumination. The excitation was filtered with an interference filter with a bandpass of 460–485 nm. The emission was collected with a 40x objective and passed through a 515 nm barrier filter. The emission was recorded with a video camera head with a chalnicon tube, digitized and stored by a Hamamatus video image processor under the control of a VaxStation II computer. This procedure was repeated under phase illumination so that the boundaries of the cell could be accurately identified by phase contrast. A software program located the boundaries of the cell by identifying pixels with intensity values more than two standard deviations below the mean background pixel intensity in a manually chosen background area.

To quantify the average intensity in the cell cytoplasm, the mean background value ($B_m$) was subtracted from the entire image including the pixel values in the cell ($P_i$). Since the background intensity could be used as a measure of the excitation intensity, the net pixel values within the boundaries of the cell were normalized to $B_m$. To normalized pixel values were then summed, and that sum was normalized to the area of the cell (A). This result was termed the intensity of the cell $I_c$:

$$I_c = \Sigma_i (P_i - B_m)/B_m A$$

$I_c$ was determined for each of the 50 cells, 25 from each of two simultaneously-removed coverslips. The standard deviation and means were then calculated. The mean for two coverslips was plotted at each time point (2, 4 and 6 hours) This process was carried out for both the experimentals and controls at each time point.

Results

Exocytosis

Figure 4:
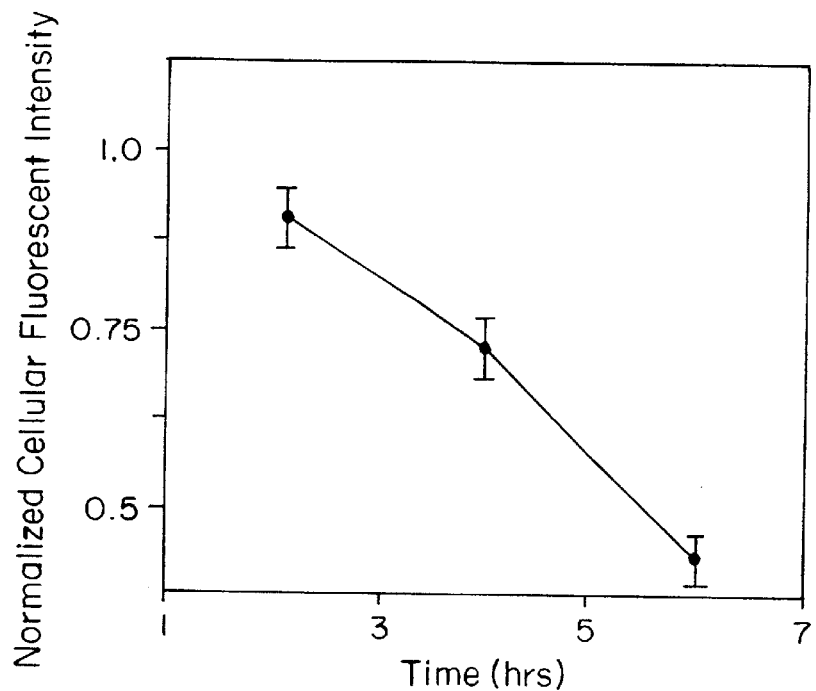
FIG. 4 is a graphic representation of the rate of exocytosis in human dermal fibroblasts in monolayer culture as a function of cellular fluorescence verses exposure time. Release of Lucifer Yellow CH form secretory vesicles in fibroblasts into the extracellular space is indicated by cellular fluorescence vs. time after dye loading. Loss of fluorescence occurs via exocytosis. Approximately 55% of the dye is secreted in 6 hours.
Figure 5:
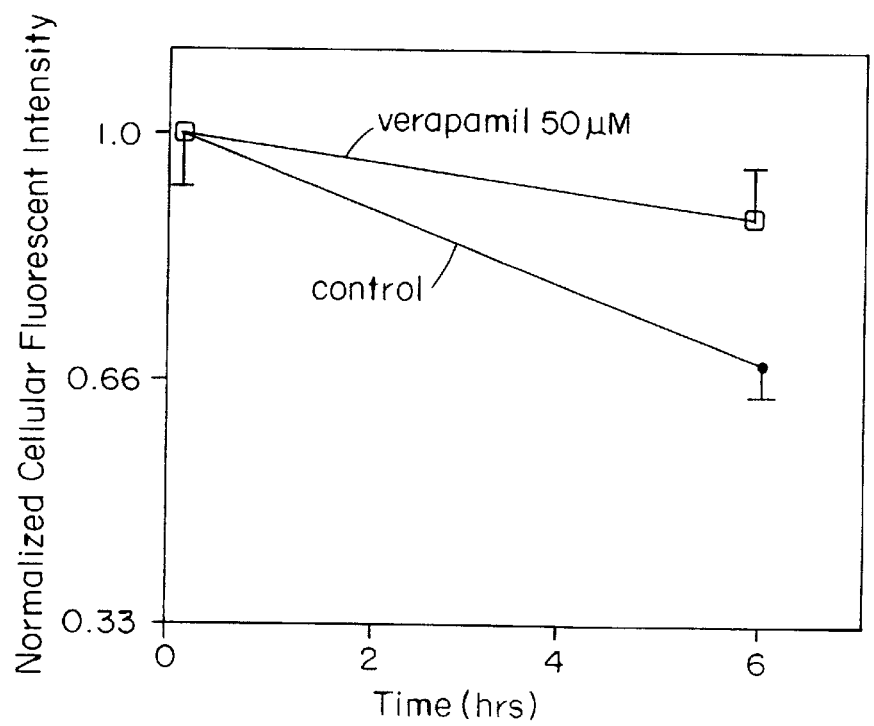
FIG. 5 is a graphic representation of the effect of the calcium antagonist verapamil (50 $\mu$M) on release of Lucifer Yellow CH from human dermal fibroblasts in monolayer culture. Retardation of exocytosis is demonstrated.

Exocytosis was observed to proceed at a near constant rate over a six hour period of observation in human dermal fibroblasts in monolayer culture (FIG. 4). The rate of exocytosis of Lucifer yellow dextran was found to be sensitive to plasma membrane calcium channel function. Both verapamil (10 $\mu$M) and nifedipine (100 $\mu$M) were found to significantly retard exocytosis over a six hour period in these cells (FIG. 5 and Tables II and III). These results clearly demonstrate that exocytosis in human fibroblasts can be regulated. In FIG. 5, the controls are represented by the squares. Table II and III show the retardation of exocytosis in human dermal fibroblasts by calcium channel blockers, verapamil (50 $\mu$M) and nifedipine (1 $\mu$M) respectively.

TABLE II

Effect of Verapamil on Exocytosis Response

| Stimulus | Exposure Time Hours | Average Intensity | Standard Error | Intensity Difference | p value |
|---|---|---|---|---|---|
| Control | 0 | 855 | 38 | | |
| | 6 | 691 | 23 | | |
| Verapamil 50 $\mu$M | 6 | 793 | 35 | 14.8% | p < 0.02 |

TABLE III

Effect of Nifedipine on Exocytosis Response

| Stimulus | Exposure Time (Hours) | Average Normalized Intensity | Standard Error | p value |
|---|---|---|---|---|
| Control | 0 | .58 | .029 | |
| | 4 | .54 | .029 | |
| | 6 | .36 | .015 | |
| Nifedipine: 1 $\mu$M | 4 | .58 | .029 | p > 0.05 |
| | 6 | .49 | .047 | p > 0.03 |

EXAMPLE 4

Study on Cell Share Changes Caused by Calcium Antagonists

Light and electron microscopy studies indicated that verapamil caused the cells to adopt a more rounded shape than controls. These rounded cells were tested for viability by staining the cells with 0.01% trypan blue for 5 minutes. Most of the cells were not stained with trypan blue indicating that the cell membranes were intact and cells remain viable. Again, alteration of cell shape correlates with the change in cell programming from biosynthetic mode to a degradative mode. Based upon this observation, it is hypothesized that calcium channel blockers drive the cells toward matrix degradation, perhaps mediated by cell shape changes.

EXAMPLE 5

Studies of the Effect of Verapamil in Conjunction with a Glucocorticoid on Human Keloid and Hypertrophic Scars.

The first patients to be tested were those patients with intractable keloids scars that had failed to respond to multiple therapeutic trails with glucocorticoids (Kenalog™). In order to determine if verapamil can induce breakdown of the scar matrix and produce macroscopic shrinkage and softening of the scar, three patients were given 1 mM verapamil in one lesion and 1 mM lidocaine in a similar lesion in the same or contralateral area of the body.

The response to the initial injection of verapamil was dramatic softening of the scars. The lidocaine did not produce softening of the scars. On subsequent injection of verapamil at biweekly intervals, the response of keloid scars was to return gradually towards the original stiffness of the scar. However, in patients with hypertrophic scars, the response to verapamil therapy was equally effective on the first injection, but these scars differed from keloid scars in that further injection led to further softening and fading of the scars.

Dramatic results have occurred in patients with burn scar contractures. In two patients injected with verapamil alone, the scar contracture disappeared in two-to-three weeks. Results for other diagnoses were also positive One patient with a hypertrophic scar on the volar surface of the wrist received verapamil injections into the scar site, causing a 10–30 reduction in the scar size and rapid fading of the scar. Another with hypertrophic scars on the right wrist and knee experienced rapid fading and shrinkage of scars with verapamil injections. Verapamil injections into a scar contracture of the joints on the hand of another individual allowed a, substantial increase in range of motion by 15–20 degrees, and decreased hard edema. A patient whose left had and right palm were affected by Dupuytren's disease experienced softening of the areas after one verapamil injection; finger extension was also increased by 10 degrees Equivalents Those skilled in the art will recognize, or be able to ascertain using no more than routine experimentation, many equivalents to the specific embodiments of the invention described specifically herein. Such equivalents are intended to be encompassed in the scope of the following claims:

I claim:

1. A composition comprising an effective amount of a calcium antagonist and protein synthesis inhibitor sufficient to cause matrix degradation at a scar site so as to control scar formation and reduce preexisting scar tissue caused by excessive fibroblast biosynthesis at the scar site in a mammal, in a physiologically acceptable vehicle.

2. The composition of claim 1, wherein the calcium antagonist is a calmodulin inhibitor, a Protein Kinase C inhibitor or a calcium transport blocker.

3. The composition of claim 2, wherein the calcium transport blocker is selected from the group consisting of phenylalkylamine compounds, dihydropyridine compounds, benzothiazepine compounds and biologically compatible polyvalent salts.

4. The composition of claim 2 wherein the calcium transport blocker is selected from the group consisting of verapamil, nifedipine, nicardipine, nimodipine, diltiazem, cobalt chloride and nickel chloride.

5. The composition of claim 1, wherein the protein synthesis inhibitor is a steroid.

* * * * *